United States Patent [19]

Nishikawa et al.

[11] Patent Number: 5,874,271
[45] Date of Patent: Feb. 23, 1999

[54] HUMAN GLYCOSYLTRANSFERASE GENE, COMPOUNDS AND METHOD FOR INHIBITING CANCEROUS METASTASIS

[75] Inventors: Atsushi Nishikawa, Toyonaka; Yoshito Ihara, Mino; Masafumi Yoshimura, Osaka; Shunichiro Taniguchi, Fukuoka-ken; Naoyuki Taniguchi, Toyonaka, all of Japan

[73] Assignee: Takara Shuzo Co., Ltd., Japan

[21] Appl. No.: 524,828

[22] Filed: Sep. 7, 1995

Related U.S. Application Data

[63] Continuation-in-part of Ser. No. 107,173, Aug. 17, 1993, abandoned.

[30] Foreign Application Priority Data

Aug. 21, 1992 [JP] Japan ..................................... 4-243984
Oct. 12, 1994 [JP] Japan ..................................... 6-271802

[51] Int. Cl.[6] .............................. C12N 9/10; C12N 1/20
[52] U.S. Cl. ................ 435/193; 435/252.3; 435/252.33; 435/365; 536/23.1; 536/23.2; 536/23.5
[58] Field of Search .................................. 435/69.1, 193, 435/240.2, 252.3, 320.1, 252.33, 365; 536/22.1, 23.1, 23.2, 23.5

[56] References Cited

FOREIGN PATENT DOCUMENTS

WO9209694  6/1992  WIPO .

OTHER PUBLICATIONS

J. Boichem, vol. 113, No. 6, Jun. 1993, Tokyo, p. 6920698, Y. Ihara et al., "cDNA Cloning Expression and Chromosomal Localization of Human GnT–III".

J. Biol. Chem., vol. 167, No. 25, 5, Sep. 1992, pp. 18199–18204, A. Nishikawa et al., "Purification, cDNA Cloning and Expression of GnT–III From Rat Kidney".

Biochem, Biophys. Res. Commun., vol. 172, No. 3, 15 Nov. 1990, pp. 1260–1266, H. Nakao et al., "Modulation of Gnt, III, IV, V Activities And . . . ".

Clin. Chim. Acta., vol. 185, No. 3, 15 Dec. 1989, pp. 325–332, K. Ishibashi et al., "GnT–III In Human Serum and Liver and Hepatoma Tissues . . . ".

The Journal of Biological Chemistry, vol. 267. pp. 18199–18204 (1992), "Purification, cDNA Cloning, and Expression of UDP–N–acetylglucosamine: β–D–mannoside β–D–mannoside β–1, 4N–Acetylglucosaminyltransferase III from Rat Kidney".

*Primary Examiner*—Robert A. Wax
*Assistant Examiner*—Nashaat T. Nasheed
*Attorney, Agent, or Firm*—Wenderoth, Lind & Ponack

[57] ABSTRACT

A gene encoding human glycosyltransferase (human GnT-III) and recombinant DNA method for producing the enzyme are provided. A cancerous metastasis inhibitor comprising GnT-III, or a gene thereof, and a method of inhibiting cancerous metastasis in a mammal are also provided.

6 Claims, 7 Drawing Sheets

HUMAN GLYCOSYLTRANSFERASE GENE, COMPOUNDS AND METHOD FOR INHIBITING CANCEROUS METASTASIS

REFERENCE TO RELATED APPLICATIONS

This is a continuation-in-part of U.S. application Ser. No. 08/107,173, which was filed on Aug. 17, 1993, now abandoned.

FIELD OF THE INVENTION

This invention relates to a human glycosyltransferase gene and a process for producing the transferase which is useful in the field of sugar engineering. This invention also relates to a drug by which the activity of a specific enzyme in cancer cells or nearby tissues is increased, thereby inhibiting metastasis of the cancer.

BACKGROUND OF THE INVENTION

UDP-N-acetylglucosamine:β-D-mannoside β1 -4N-acetyl-glucosaminyltransferase III (EC 2.4.1.144: hereinafter referred to simply as GnT-III), which is an enzyme that transfers a GlcNAc residue in UDP-N-acetylglucosamine (UDP-GlcNAc) to a mannose (Man) residue forming a β1-4 bond in an asparagine binding type sugar chain, was reported for the first time by Narasimhan [see Journal of Biological chemistry, 257, 10235–10242 (1982)]. The GlcNAc transferred by GnT-III, which is called a bisecting GlcNAc, has been found in the sugar chains of various glycoproteins. It has been further reported by Narasimhan et al. [see J. Biol. Chem., 263, 1273–1282 (1988)] and Pascale et al. [see Carcinogenesis, 10, 961–964 (1989)] that the activity of GnT-III increases in rat liver accompanying its canceration.

In addition, Ishibashi et al. have reported an increase in the activity of GnT-III in the serum of a human patient with hepatic cancer [see Clinica Chimica Acta, 185, 325–332 (1989)].

Regarding genes, furthermore, a gene coding for GnT-III originating in rat (rat GnT-III) has been isolated by one of the present inventors [see Japanese Patent Application No. 69345/1992]. It is believed that metastasis is the main problem in clinical medicine for cancer. Namely, metastasis means a phenomenon where cancer cells from a primary tumor enter into the blood system or the lymphatic system and form a new tumor in another part of the body via such a system. If cancer cells do not metastasize or the cancerous metastasis can be prevented, a patient with cancer can be saved by excising the cancer.

It has been clarified that, in many solid cancers, sugar chain structures expressed on the surfaces of cancer cells vary as the cancer advances, i.e., depending on the stage of the advance and the occurrence of the metastatic character. It is therefore considered that the sugar chain structures on the surface of the cancer cells vary as the cancer advances and is acquire metastatic character. In particular, it has been widely known that a cell having a sugar chain with a specific branched structure expressed thereon has a potent ability to metastasize as reported by Dennis et al. [Science, 236, 582–585 (1987)]. The evidence thereof is as follows:

1) A leukoagglutinin originating in kidney bean (L-PHA) recognizes an asparagine linked sugar chain having a Galβ1-4GlcNAcβ1-6(Galβ1-4GlcNAcβ1-2)- Manα1 branched structure and binds thereto. A mouse cancer cell line MDAY-D2, which shows a sensitivity to this L-PHA, has metastatic potential. On the other hand, a cell line showing a resistance to L-PHA has low metastatic potential. 2) An L-PHA binding type glycoprotein is detected from the cell membrane of a metastatic cell line, while no L-PHA binding type glycoprotein is detected from the cell membrane of a cell line having low metastatic potential. The incidence of the metastasis correlates to the occurrence of the L-PHA binding type glycoprotein.

3) When an oncogene is introduced into rat cells, the L-PHA binding type glycoprotein appears therein. When these cells are injected into a nude mouse, a tumor is formed and metastasizes.

The results of tissue staining with L-PHA indicate that the L-PHA binding type sugar chain appears not only in cancer cells which have been experimentally formed but also in human breast cancer and colon cancer and that the intensity of the L-PHA staining is elevated as the cancer advances [Cancer Research, 51, 718–723 (1991)].

Since a sugar chain is not a direct product of a gene, a change in the sugar chain structure depends on a glycosyltransferase. It has been reported that a mouse cell line having the L-PHA binding type sugar chain expressed thereon and showing metastatic potential has a higher activity of N-acetyl-glucosaminyltransferase (GnT) V (hereinafter referred to simply as GnT-V), which forms GlcNAcβ1-6Manα1 branching, than a cell line showing low metastatic potential [Science, 236, 582β585 (1987)]. Also, the intensity of L-PHA staining positively correlates to the GnT-V activity in a human breast cancer tissue [Cancer Research, 49, 945–950 (1989)].

As described above, there have been detailed studies on the relationship between the appearance of the L-PHA binding type sugar chain having the GlcNAcβ1-6Manα1-branched structure and the metastatic character of cancer cells. However it has not been revealed so far whether or not the sugar chain on the surface of the cell having such a structure specifies the extent of the advance of the cancer and directly causes the acquisition of the metastatic character. Needless to say, there has been developed neither a method nor a drug whereby the possibility of cancerous metastasis can be effectively reduced.

In the process of the studies relating to structural changes in sugar chains on the surface of cells, the present inventors have successfully acquired rat and human GnT-III genes (Japanese Patent Laid-Open No. 38767/1994 and U.S. patent appln. Ser. No. 08/107,173). This enzyme forms the GlcNAcβ1-4Manβ1 structure of an asparagine linked sugar chain, i.e., the so-called bisecting GlcNAc. It has been reported that the activity of this GnT-III also increases in cancer cells. In particular, the present inventors have clarified that the activity of this enzyme increases in rat or human liver cancer tissues or the serum of a patient with liver cancer [Biochemical and Biophysical Research Communications, 152, 107–112 (1988); and Clinica Chimica Acta, 185, 325–332 (1989)]. Regarding cancers other than liver cancer, it has also been reported that GnT-V and GnT-III activities increase in cells which have been malignantly transformed by introducing N-ras protooncogene thereinto [Journal of Biological Chemistry, 266, 21674–21680 (1991)] and that GnT-III activity largely increases in metastatic prostatic cancer cells [FEBS Letters, 308, 46–49 (1992)].

OBJECT OF THE INVENTION

As described above, GnT-III plays an important role in vivo and is a highly useful enzyme in the diagnosis of cancer because its activity increases accompanying canceration.

However reports on human GnT-III have been limited to the determination of its activity and there has been no report of isolation of a human GnT-III gene so far.

The present invention aims to isolate a human GnT-III gene and provide a genetic engineering process for producing human GnT-III.

As described above, it is known that a sugar chain structure on the surface of cancer cells is changed or a glycosyltransferase in cancer cells is activated as the cancer advances or acquires the metastatic character. However, there has been developed no cancerous metastasis inhibitor with the use of these phenomena as the site of action.

It is a further object of the present invention to provide a drug for inhibiting cancerous metastasis by increasing the activity of a specific glycosyltransferase in cancer cells or nearby tissues.

SUMMARY OF THE INVENTION

The present invention can be summarized as follows. The present invention relates to a human glycosyltransferase gene. The present invention also relates to a process for producing a human glycosyltransferase.

The present inventors have prepared a probe from a rat GnT-III gene, screened a human cDNA library for clones containing a gene coding for human GnT-III by using this probe, and succeeded in the isolation of the gene coding for human GnT-III and the expression of human GnT-III with the use of this gene.

The present invention also relates to a cancerous metastasis inhibitor which comprises GnT-III or its gene as the active ingredient.

The present inventors have conducted extensive studies on the relationship between the metastatic character of cancer cells and a change in the sugar chain structure on the surface of the cells. As a result, they have surprisingly found that the ability of cancer cells to metastasize can be unexpectedly inhibited by introducing GnT-III, which is expressed specifically in cancer cells and the activity of which has been considered as rather positively correlating to the extent of the advance of cancer into cancer cells, thus completing the present invention.

The invention will now be described in more detail, with reference to the following examples and drawings.

DETAILED DESCRIPTION OF THE INVENTION

Examples of the probe which can be used in the detection of a gene coding for human GnT-III include a DNA fragment of approximately 1.4 kb which is obtained by cleaving a plasmid SV3 containing the rat GnT-III gene described in the Japanese Patent Application No. 69345/1992 with a restriction enzyme HindIII. The plasmid SV3 can be prepared from *Escherichia coli* XL1-Blue SV3 (FERM BP-4325) which has been deposited with Fermentation Research Institute, Agency of Industrial Science and Technology. By using this DNA fragment as a probe, for example, a commercially available human cDNA library can be screened for a gene coding for human GnT-III by plaque hybridization. As a result of the screening, two positive clones were obtained from $3 \times 10^6$ plaques and respectively named H2 and H3. These clones were digested with EcoRI and then subcloned into, for example, the EcoRI site of Bluescript IISK$^+$ (Stratagene). These subcloned plasmids were named respectively pBluescript II (H2) and pBluescript II (H3).

Figure 2:
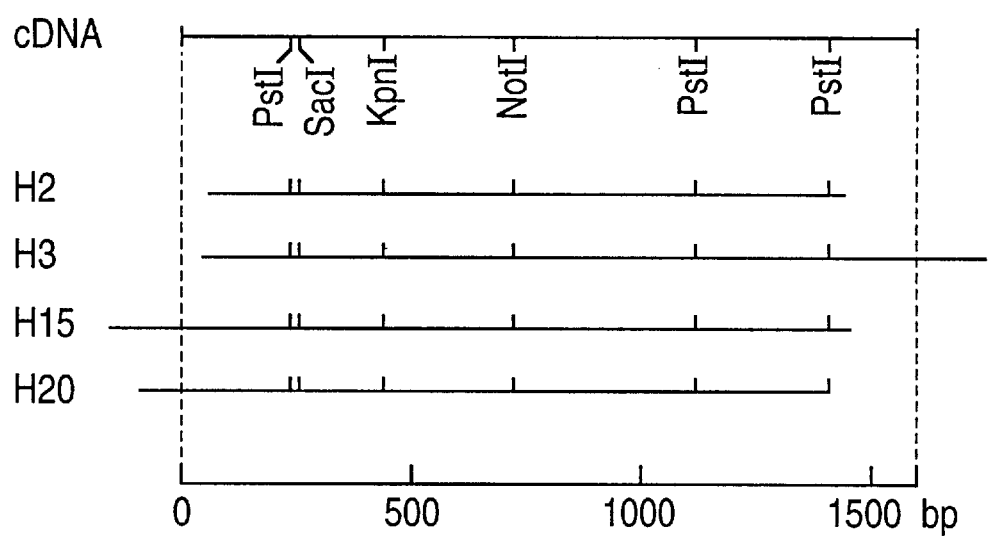
FIG. 2 shows the relationships among four DNAs H2, H3, H15 and H20.

FIG. 2 shows a relationship between H2 and H3 revealed by analyzing with restriction enzymes. Examination of the base sequences of the H2 and H3 plasmids reveals that no initiator codon ATG is involved therein. In order to obtain a full-length gene coding for human GnT-III, therefore, screening of the human cDNA library is effected again with the use of H2 and H3 as a probe. As a result, four positive clones were obtained from $7 \times 10^5$ plaques. These clones were digested with EcoRI and then subcloned into, for example, the EcoRI site of Bluescript IISK$^+$.

From among the subcloned DNAs, two DNAs containing an initiator codon are named respectively H15 and H20. The plasmids having H15 and H20 subcloned therein are named respectively pBluescript II (H15) and pBluescript II (H20). FIG. 2 shows a relationship between H15 and H20 revealed by analyzing with restriction enzymes.

Figure 3:
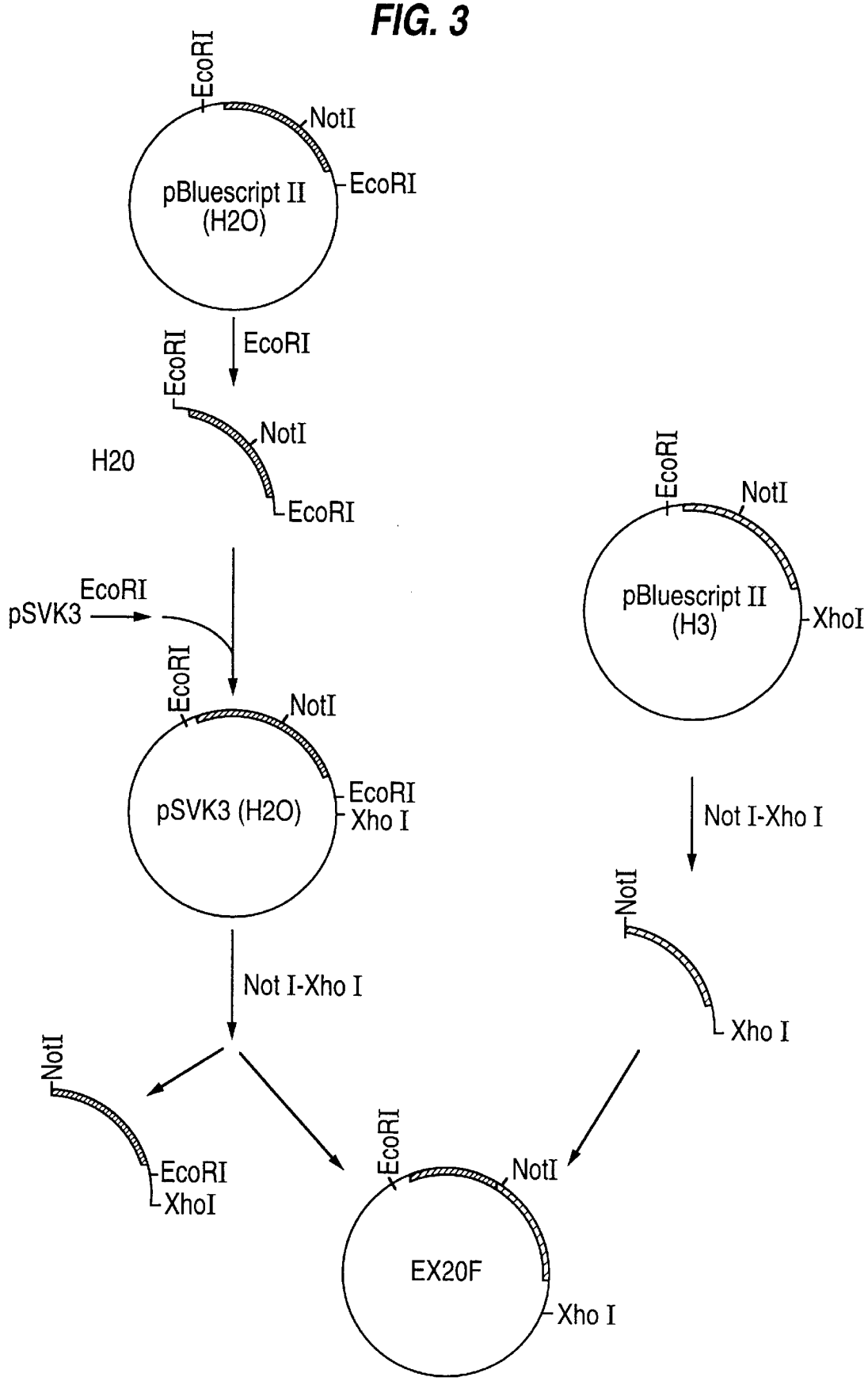
FIG. 3 depicts the construction of plasmid EX20F.

Next, an expression plasmid containing a full-length human GnT-III gene can be constructed by, for example, excising H20 from pBluescript II (H20) with ECORI and integrating it into pSVK3 (Pharmacia) to prepare pSVK (H20). Further, a fragment excised from pBluescript II (H3) having H3 integrated thereinto with NotI and XhoI is integrated into the pSVK(H20) in such a manner as to replace the NotI-XhoI fragment of the pSVK(H20) therewith, thus constructing an expression plasmid EX20F (see FIG. 3).

Figure 1:
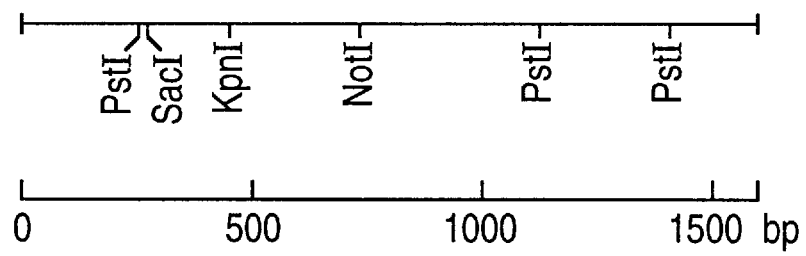
FIG. 1 shows a restriction map of a gene coding for human GnT-III.

The base sequence of the DNA fragment integrated into EX2OF can be determined by the dideoxy method. SEQ ID NO. 1 in the sequence listing shows a part of the base sequence thus determined. As the result of screening of an open reading frame (ORF), an ORF is found in bases Nos. 169 to 1761. FIG. 1 shows a restriction map of this ORF region. SEQ ID NO. 2 in the sequence listing shows the base sequence and the deduced amino acid sequence of the ORF region.

Human GnT-III producing cells can be obtained by transforming expression cells by an expression plasmid and examining the capability of the transformant to express human GnT-III. Examples of usable expression cells include COS-1 cells (ATCC CRL 1650). For example, the COS-1 cells can be transformed by the above expression plasmid EX20F. Then the transformant is incubated and the activity of GnT-III expressed in the transformant is determined to specify a gene coding for human GnT-III. This gene is integrated into EX2OF and a part of its base sequence is located on a DNA fragment represented by SEQ ID NO. 1. Human GnT-III can be produced by genetic engineering technique by incubating the above transformant.

By effecting hybridization with the use of the gene thus obtained as a probe under stringent conditions, it is anticipated that genes for enzymes analogous to that of the present invention, which are different therefrom in sequence but expected to have a similar activity, may be obtained. The term "under stringent conditions" as used herein means that the hybridization of a nylon membrane having DNAs immobilized thereon with the probe is conducted in a solution containing 6×SSC (1×SSC means a solution prepared by dissolving 8.76 g of sodium chloride and 4.41 g of sodium citrate in 1 liter of water), 1% of sodium lauryl sulfate, 100 µg/ml of salmon sperm DNA, and 5×Denhardt's (containing bovine serum albumin, polyvinylpyrrolidone and Ficoll each at a concentration of 0.1%) at 65° C. for 20 hours.

As described above in detail, the present invention enables a gene coding for human GnT-III to be isolated and provides a process for producing human GnT-III by using the gene. This gene and its decomposition products are usable in the determination of human GnT-III during the expression process in vivo and, therefore, are useful in the genetic diagnosis of cancer, and so forth. In addition, various antibodies can be immunologically prepared by using polypeptides coded for by the gene of the present invention. These antibodies are also useful in the field of diagnosis and for the purification of human GnT-III.

In the present invention, the object of inhibiting cancer metastasis can be achieved by introducing GnT-III into cancer cells or the tissues therearound. GnT-III may be introduced directly into the cancer cells by, for example, the microinjection method while maintaining the GnT-III activity.

Alternatively, the object of the present invention can be achieved by introducing a GnT-III gene into cancer cells with the use of, for example, a virus followed by the expression of GnT-III.

That is to say, the use of the drug of the present invention makes it possible to introduce GnT-III or a gene coding for GnT-III into cancer cells or the tissues therearound to thereby inhibit cancerous metastasis. When the cancer is located on the surface of a tissue, GnT-III or a gene coding for GnT-III may be injected directly into the affected part. Also when the cancer is located inside a tissue, GnT-III or a gene coding therefor may be injected directly into the affected part, or it is also possible to use a drug delivery system. The drug delivery system (DDS) may be selected from among commonly employed ones which are specific to cancer cells. For example, those with the use of a cancer cell receptor, a cancer-specific antibody, etc., may be used therefor. Also, it is a highly efficacious method for inhibiting cancerous metastasis to apply the drug of the present invention to the tissues around the affected part at the enucleation of a cancer tissue.

In the application of the drug of the present invention comprising GnT-III or a gene thereof to cancer cells or the tissues therearound, it is a matter of course to endeavor to utilize its efficacy to the full.

The cancerous metastasis inhibitor of the present invention may be processed into a preparation in the same manner as those employed for the production of usual drugs for gene therapy or preparations containing proteins, so long as it contains GnT-III or a gene thereof in an amount falling within a pharmaceutically acceptable range. The preparation may further contain carriers, fillers, stabilizers, thickening agents, etc.

The dose of GnT-III or a gene thereof to be used as the cancerous metastatis inhibitor of the present invention may be appropriately regulated by considering the conditions (age, body weight, etc.) of the patient and the stage of the affected part.

GnT-III or a gene thereof contained in the cancerous metastasis inhibitor of the present invention is a substance occurring in vivo and thus having no toxicity.

The enzymological properties of GnT-III to be used in the present invention have been already clarified in detail. This enzyme can be prepared from, for example, rat kidney in accordance with the method shown in Table 1.

TABLE 1

| Step | Specific activity (nmol/mg/hr) |
| --- | --- |
| 1. homogenate | 2.16 |
| 2. Triton extract | 8.94 |
| 3. QAE-Sepharose | 42.1 |
| 4. Hydroxyapatite | 74.6 |
| 5. $Cu^{2+}$-chelating Sepharose | 248 |
| 6. Con A Sepharose | 578 |
| 7. $Cu^{2+}$-chelating Sepharose | 820 |
| 8. UDP-hexanolamine agarose | 7,230 |
| 9. Gn, Gn-bi-Asn Sepharose | 331,000 |

In Table 1, Gn, Gn-bi-Asn represents GlcNAcβ1-2Manα1 -6 (GlcNAcβ1-2Manα1-3)Manβ1- 4GlcNAcβ1-4GlcNAc-Asn. The GnT-III activities are measured in accordance with the method described in Biochimica et Biophysica Acta, 1035 (3), 313–318 (1990) by using 80 µM of a fluorescent substrate. The specific activities of the enzyme are expressed in GlcNAc (mol) transferred/protein (mg)/time (hr) by using pyridyl(-2-) aminated GlcNAc as a standard. The protein is assayed by using a BCA kit (mfd. by Pierce) with the use of serum albumin as a standard.

The gene of GnT-III may be obtained from, for example, a human fetal liver cDNA library in accordance with the method of Ihara et al. [Journal of Biochemistry, 113, 692–698 (1993)]. Also, a gene obtained from, for example, a rat liver CDNA library in accordance with the method of Nishikawa et al. [Journal of Biological Chemistry, 267, 18199–18204 (1992)] can be appropriately used as an experimental material in studying the inhibition of cancerous metastasis.

Further, rat GnT-III may be prepared by, for example, the method described in Japanese Patent Laid-Open No. 38767/1994 with the use of FERM BP-4352.

Furthermore, human GnT-III may be prepared by, for example, the method described in US Patent Appln. Serial No. 08/107,173.

The DNA sequence of a gene coding for rat GnT-III and the amino acid sequence thereof are represented by SEQ ID No. 3 of the Sequence Listing. The DNA sequence of a gene coding for human GnT-III and the amino acid sequence thereof are represented by SEQ ID No. 2 of the Sequence Listing. By using such a gene as a probe, a gene which codes for a protein having GnT-III activity and is hybridizable with the above- mentioned gene can be prepared. Alternatively, the gene represented by SEQ ID No. 3 or 2 of the Sequence Listing may be subjected to, for example, genetic engineering replacement, mutation or cleavage to thereby prepare a gene which codes for a protein having GnT-III activity and is hybridizable with the above-mentioned gene.

These genes and the expression products thereof are also usable as a drug of the present invention.

When GnT-III of the drug of the present invention is to be introduced into cells by using a gene per se, the GnT-III gene can be easily introduced into the cells by using a recombinant vector having the GnT-III gene and a regulator gene relating thereto. Thus, use can be made of not only a promoter of GnT-III per se but also other effective promoters such as an SV40 promoter, an LTR promoter from a retro virus, a heat shock promoter, a metallothionein promoter and an actin promoter.

In the introduction of the GnT-III gene, a cancer tissue or an uncancerized tissue can be efficiently infected with a vector containing this gene by using a virus vector. As such a vector, use can be made of a virus which has been known as transporting the target DNA and having a high infection efficiency, such as a retro virus, vaccinia virus, adenovirus or a nonproliferative recombinant virus. Among these viruses, a nonproliferative recombinant virus, which would not proliferate after the introduction into the target cells and thus should be renewed at intervals, of two weeks to two months, has a merit that its amount can be controlled each time. Also, liposomes, i.e., artificial lipid capsules may be used therefor.

A vector which is desirable as the drug of the present invention may be constructed by the following method. The cDNA of human GnT-III is introduced into the EcoRI site of a pCAGGS vector (FIG. 8) provided by Dr. Kenichi Yamamura, Kumamoto University, to thereby form an expression vector of GnT-III regulated by an actin promoter.

Regarding cancerous metastasis, the possibility of metastasis can be evaluated by, for example, measuring the activity of the treated cells to form metastatic nodes in mouse lungs. More specifically, a DNA obtained by linearizing the above-mentioned expression vector of GnT-III with SalI is mixed with another DNA obtained by linearizing pSV2-neo [Japanese Cancer Research Bank, a vector having a neomycin (G418)-tolerant gene] with BamHI (mfd. by Takara Shuzo Co., Ltd.) at a ratio of 10:1 and then introduced into mouse melanoma cells by the electroporation method. After incubating in a medium containing the antibiotic G418, tolerant cell lines are screened therefrom. Several cell lines expressing the GnT-III activity thus obtained are selected and incubated to give the semiconfluent state. Then cells are peeled off the plate and collected to thereby prepare cell suspensions. Each cell suspension is then intravenously injected into the tails of a group of seven C57BL/6 mice aged 5 weeks. After 21 days, the lungs are taken out and melanoma colonies are counted to thereby evaluate the ability of the cancer cells to metastasize. Alternatively, the ability of the cancer cells to metastasize can be evaluated by examining the mobility of the cells in vitro by, for example, the Matrigel assay method with the use of a Matrigel invasion chamber [Cancer Research, 52, 3610 (1992)].

Thus the present inventors have compared the ability of the mouse melanoma cells having the GnT-III gene introduced therein to metastasize with that of cells having no GnT-III gene. As a result, they have found that cells having the GnT-III gene introduced thereinto clearly show a decrease in the metastatic potential thus completing the present invention.

The drug of the present invention is useful in the field of cancer therapy.

To further illustrate the present invention in greater detail, but not by way of limitation, the following Examples are presented.

Example 1

(1) Screening of cDNA library

SV3 was prepared from *Escherichia coli* XL1-Blue SV3 (FERM BP-4325) transformed by a plasmid SV3 and the plasmid was digested with HindIII to give a DNA fragment of approximately 1.4 kb. This DNA fragment was radiolabeled with [$\alpha$-$^{32}$P] dCTP (3000 Ci/mmol, Amersham) by using a Multiprime DNA Labeling System (Amersham) to thereby give a probe. By using the obtained probe, a human cDNA library [Human Fetal Liver <$\lambda$gtlO>, Clonetech] was screened for the target clone by plaque hybridization. As a result, two positive clones were obtained from $3 \times 10^6$ plaques. From these clones, DNAs were extracted and digested with EcoRI. The digestion products thus obtained were subcloned into Bluescript IISK$^+$ and the DNAs thus subcloned (approximately 1.3 kb and approximately 1.5 kb) were respectively named H2 and H3, while the plasmids were respectively named pBluescript II (H2) and pBluescript II (H3). FIG. 2 shows the restriction maps of these DNAs and a relationship between them.

(2) Cloning of upstream region containing initiator codon

H2 and H3 were radiolabeled in the same manner as described above to give probes. By using these probes, screening of a human cDNA library was carried out in the same manner as described above to obtain four positive clones from $7 \times 10^5$ plaques. The EcoRI-digestion products thereof were subcloned into Bluescript IISK$^+$. The base sequences of the DNAs thus subcloned were identified and two DNAS containing an initiator codon (approximately 1.6 kb and approximately 1.5 kb) were named respectively H15 and H20, while the plasmids corresponding thereto were named respectively pBluescript II (H15) and pBluescript II (H20). FIG. 2 shows the restriction maps of these DNAs and a relationship between them and H2 and H3.

Example 2

(1) Construction of expression plasmid

The pBluescript II (H20) prepared in Example 1 was digested with EcoRI to excise H20, which was integrated into the EcoRI site of an expression vector pSVK3 (Pharmacia) for eucaryotic cells to thereby give pSVK (H20). Separately, the pBluescript II (H3) prepared in the above Example 1 was digested with NotI and XhoI to obtain an NotI-XhoI fragment (approximately 0.9 kb) containing the downstream region of the human GnT-III gene. Next, an expression plasmid EX20F for eucaryotic cells was constructed by digesting pSVK(H20) with NotI and XhoI, excising the NotI-XhoI fragment away, and integrating the NotI-XhoI fragment (approximately 0.9 kb) of pBluescript II (H3) in its place (see FIG. 3).

The base sequence of the DNA fragment integrated into EX20F was determined by the dideoxy method. A part of this base sequence is represented by SEQ ID NO. 1 in the sequence listing. As the result of screening for an ORF, an ORF was found in the bases Nos. 169 to 1761. FIG. 1 shows a restriction map of this ORF region. SEQ ID NO. 2 in the sequence listing shows the base sequence and the deduced amino acid sequence of the ORF region.

(2) Transformation and expression of human GnT-III gene

The COS-1 cells to be used for expressing human GnT-III were incubated in Dulbecco's modified Eagle medium containing 10% of FCS in the presence of 5% of $CO_2$ at 37° C. under moist conditions.

Subsequently, the EX20F prepared in the above Example 2-(1) was introduced into the COS-1 cells by electroporation with the use of a Gene Pulser (Bio-Rad). More specifically, approximately $5 \times 10^6$ cells and a recombinant plasmid or a control vector were suspended in 0.8 ml of 20 mM Hepes buffer (pH 7.05) containing 137 mM of NaCl, 5 mM of KCl, 0.7 mM of $Na_2HPO_4$ and 6 mM of dextrose, and treated at a voltage of 250 V/0.4 cm and at a capacitance of 960 $\mu$F.

After the completion of the transformation, incubation was carried out for 2 days and then the cells were harvested and sonicated in PBS to determine the GnT-III activity in the sonicated cell suspension. It was found that the cells which had not been treated with the plasmid and those which had been treated with the control plasmid pSVK3 had no GnT-III activity, whereas the cells transformed by the plasmid EX20F had a GnT-III activity, suggesting that the human GnT-III gene had been expressed therein.

Thus it has been proved that a gene coding for human GnT-III exists on the DNA fragment which has been integrated into EX20F and a part of the base sequence of which is represented by SEQ ID NO. 1 in the Sequence Listing hereinafter.

(3) Determination of GnT-III activity

The GnT-III activity was determined in accordance with the description given in Biochimica et Biophysica Acta, 1035, 313–318 (1990). More precisely, by using 80 $\mu$M of pyridylamino (PA) Gn, Gn-bi [GlcNAc $\beta$1 -2Man $\alpha$1-6 (GlcNAc $\beta$1 -2Man $\alpha$1-3)Man $\beta$1-4 GlcNAc $\beta$1-4 GlcNAc-PA] as a receptor, UDP-GlcNAc serving as a sugar donor was added in such a manner as to give a final concentration of 80 $\mu$M to a 125 mM solution of 2-(N-morpholino) ethanesulfonic acid buffer (MES buffer, pH 6.25) containing 10 mM of $MnCl_2$, 200 mM of GlcNAc and 0.5% (v/v) of Triton X-100. After reacting the mixture at 37° C. for 1 hour, the GnT-III activity was determined by analyzing by HPLC.

Example 3

[Construction of expression vector and introduction thereof into cells]

The 5' noncoding region (42 bp) of a cDNA clone C4 containing the full length of a region coding for rat GnT-III [Journal of Biological Chemistry, 267, 18199–18204 (1992)] was eliminated by digesting with exonuclease III (ExoIII, mfd. by Takara Shuzo Co., Ltd.) and mung bean nuclease (mfd. by Takara Shuzo Co., Ltd.).

Figure 8:
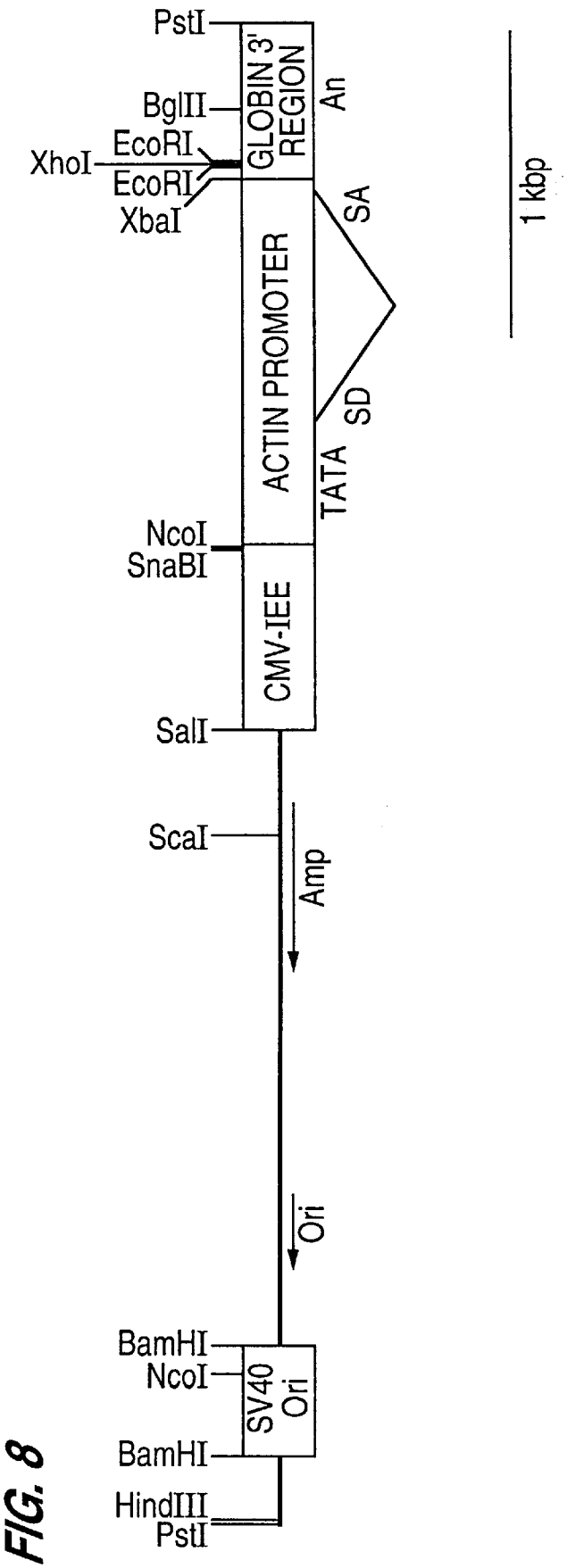
FIG. 8 shows the restriction map of a PCAGGS vector.

The C4 fragment thus shortened was digested with EcoRI (mfd. by Takara Shuzo Co., Ltd.), blunted by the Klenow treatment and then subcloned into the SmaI site of a pSVK3 vector (mfd. by Pharmacia). Then the SacI fragment was excised therefrom and blunted with T4DNA polymerase (mfd. by Takara Shuzo Co., Ltd.). Then it was subcloned into the EcoRI site of a PCAGGS vector (provided by Dr. Kenichi Yamamura, Kumamoto University) which had been similarly blunted by the Klenow treatment. FIG. 8 shows the restriction map of the PCAGGS vector.

Figure 4:
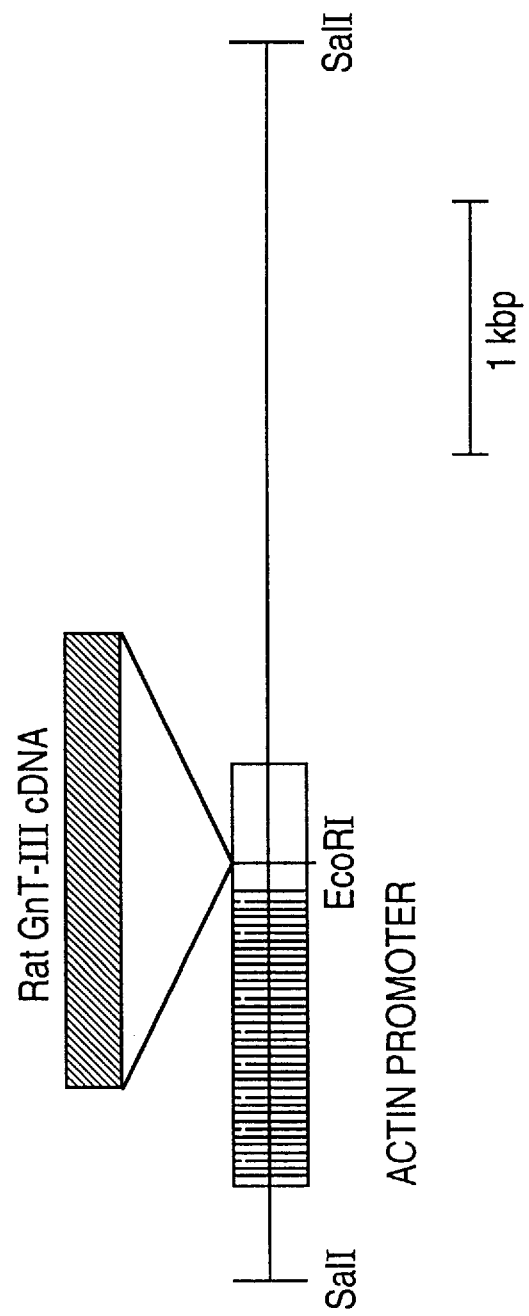
FIG. 4 is a model view of GnT-III expression plasmid Act-3.

The expression plasmid thus constructed was named GnT-III expression plasmid Act-3. In this GnT-III expression plasmid Act-3, the expression of GnT-III is regulated by an actin promoter. FIG. 4 is a model view of the GnT-III expression plasmid Act-3. In FIG. 4, the broad and solid line (black) at the upper section shows the cDNA of rat GnT-III, while the lower section shows the PCAGGS vector (FIG. 8). The hatched part in the lower section indicates the actin promoter.

This GnT-III expression plasmid Act-3 and a pSV2-neo vector [Japanese Cancer Research Bank, a vector having a neomycin (G418)-tolerant gene] were linearized by digesting respectively with SalI (mfd. by Takara Shuzo Co., Ltd.) and BamHI (mfd. by Takara Shuzo Co., Ltd.). Then 20 $\mu$g of the GnT-III expression plasmid Act-3 was mixed with 2 $\mu$g of the pSV2-neo vector and introduced into mouse melanoma B16-Fl cells by the electroporation method with the use of a Gene Pulser (mfd. by Bio Rad: voltage: 250 V/0.4 cm, electrostatic capacity: 960 $\mu$F). The cells having the gene introduced thereinto were selected on a medium containing G418 (1 mg/ml, mfd. by GIBCO BRL) and tolerant cell lines were cloned by dilution. As a result, nine cell lines having the GnT-III activity and three cell lines showing no GnT-III activity were obtained. From the cell lines having the GnT-III activity, three cell lines were arbitrarily selected and named Fl-GnT-III-1, Fl-GnT-III-2 and Fl-GnT-III 3, while two cell lines were selected from among those having no GnT-III activity and named Fl-neo-1 and Fl-neo-2.

[Enzyme activities of GnT-III and GnT-V of cells]

Table 2 presented herein shows the GnT-III, GnT-V and galactosyl- transferase (Gal-T) activities in the cells, the number of copies of the GnT-III gene introduced thereinto, the proliferation rates and the abilities to form colonies.

In Table 2, "a" indicates the activities of the enzymes GnT-III, GnT-V and Gal-T determined by using a sugar chain fluorolabeled with 2-aminopyridine as a substrate in accordance respectively with the methods described in Analytical Biochemistry, 170, 349–354 (1988), Methods in Enzymology, 179, 397–408 (1985) and Journal of Biological Chemistry, 265, 6009–6018 (1990). In Table 2, "b" indicates the numbers of copies of the introduced GnT-III gene measured by the Southern blot technique, while "c" indicates the proliferation rates and the abilities to form colonies of the cells which had been determined by repeating the test thrice. Also, "d" and "e" give the results of statistical treatment according to Student's t test, showing possibilities [d]p<0.001 and [e]p<0.05 each for B16-Fl. The expression "p<0.001" means being identical with B16-Fl at a possibility lower than 0.001.

| Cell | Enzyme activity (pmol/h/mg)[a] | | | Number of copies of GnT-III gene introduced[b] | Proliferation rate[c] | Ability to form colonies[c] |
| --- | --- | --- | --- | --- | --- | --- |
| | GnT-III | GnT-V | Gal-T | | | |
| Fl | not detected | 758 ± 35 | 2,150 ± 188 | not detected | 100 | 116 ± 7 |
| Fl-neo-1 | not detected | 743 ± 222 | 1,760 ± 189 | not detected | 122 ± 10 | 69 ± 8[e] |
| Fl-neo-2 | not detected | 861 ± 74 | 1,410 ± 267 | not detected | 107 ± 11 | 82 ± 8 |
| Fl-GnT-III-1 | 125,000 ± 12,000[d] | 1,080 ± 61 | 2,720 ± 632 | 1 | 80 ± 13 | 128 ± 7 |
| Fl-GnT-III-2 | 164,000 ± 5,200[d] | 1,350 ± 112 | 2,840 ± 329 | 2 | 119 ± 13 | 102 ± 10 |
| Fl-GnT-III-3 | 92,100 ± 3,070[d] | 1,280 ± 158 | 1,990 ± 293 | 2 | 86 ± 10 | 58 ± 7[e] |

As Table 2 shows, the GnT-III activity was elevated to 92,100 to 164,000 pmol/h/mg protein in the GnT-III positive cells. On the other hand, the GnT-V and Gal-T activities of the transformed cell lines were scarcely different from those of the parent cell line.

Figure 5:
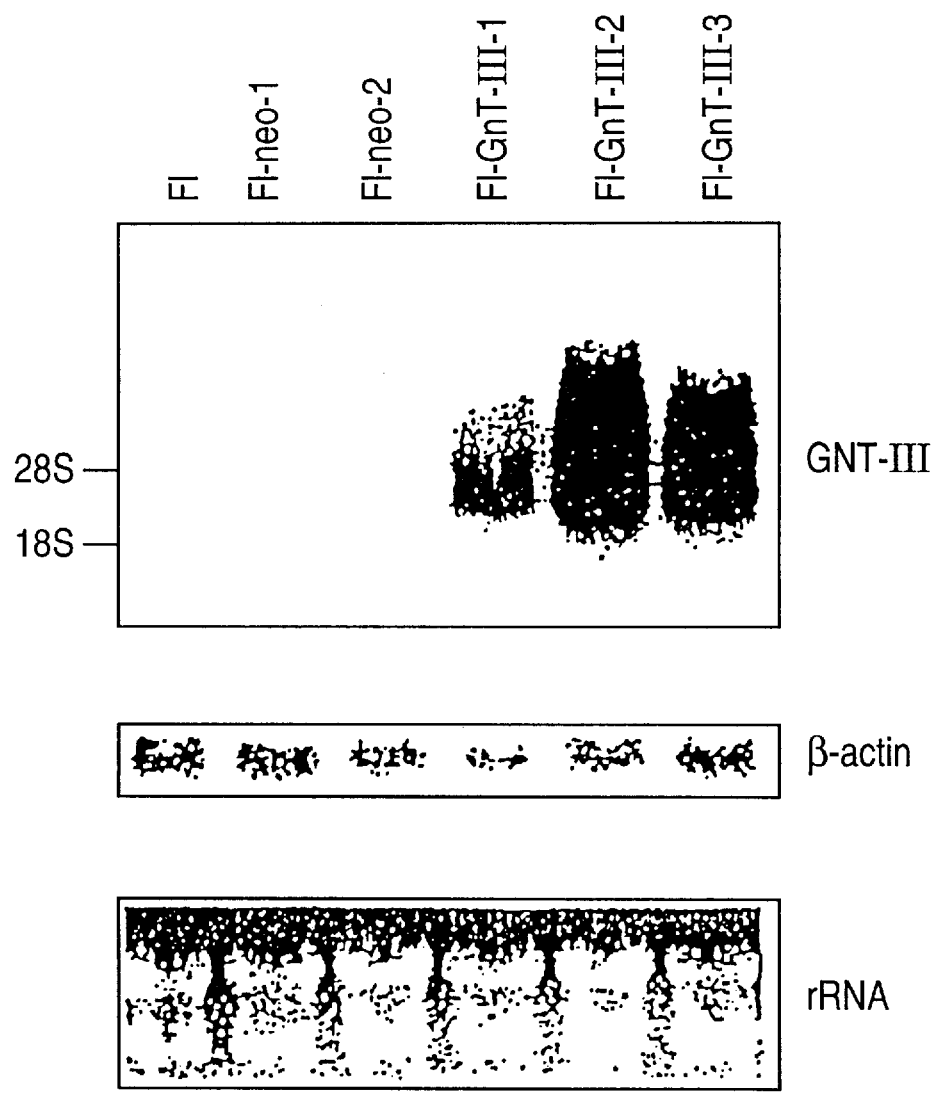
FIG. 5 shows the amount of a GnT-III transcript (MRNA) in B16-Fl cells.

The amount of the GnT-III transcript (mRNA) in the B16-Fl cells was determined. FIG. 5 shows the amount of the GnT-III transcript (mRNA) in the B16-Fl cells. The amounts of the GnT-III transcript (mRNA), $\beta$-actin and ribosomal RNA (rRNA) are shown respectively in the upper, middle and lower sections. Fl-GnT-III-2 shows the maximum level of the mRNA of GnT-III, while Fl-GnT-III-1 shows the minimum level thereof.

[Evaluation of cancerous metastasis]

Figure 6:
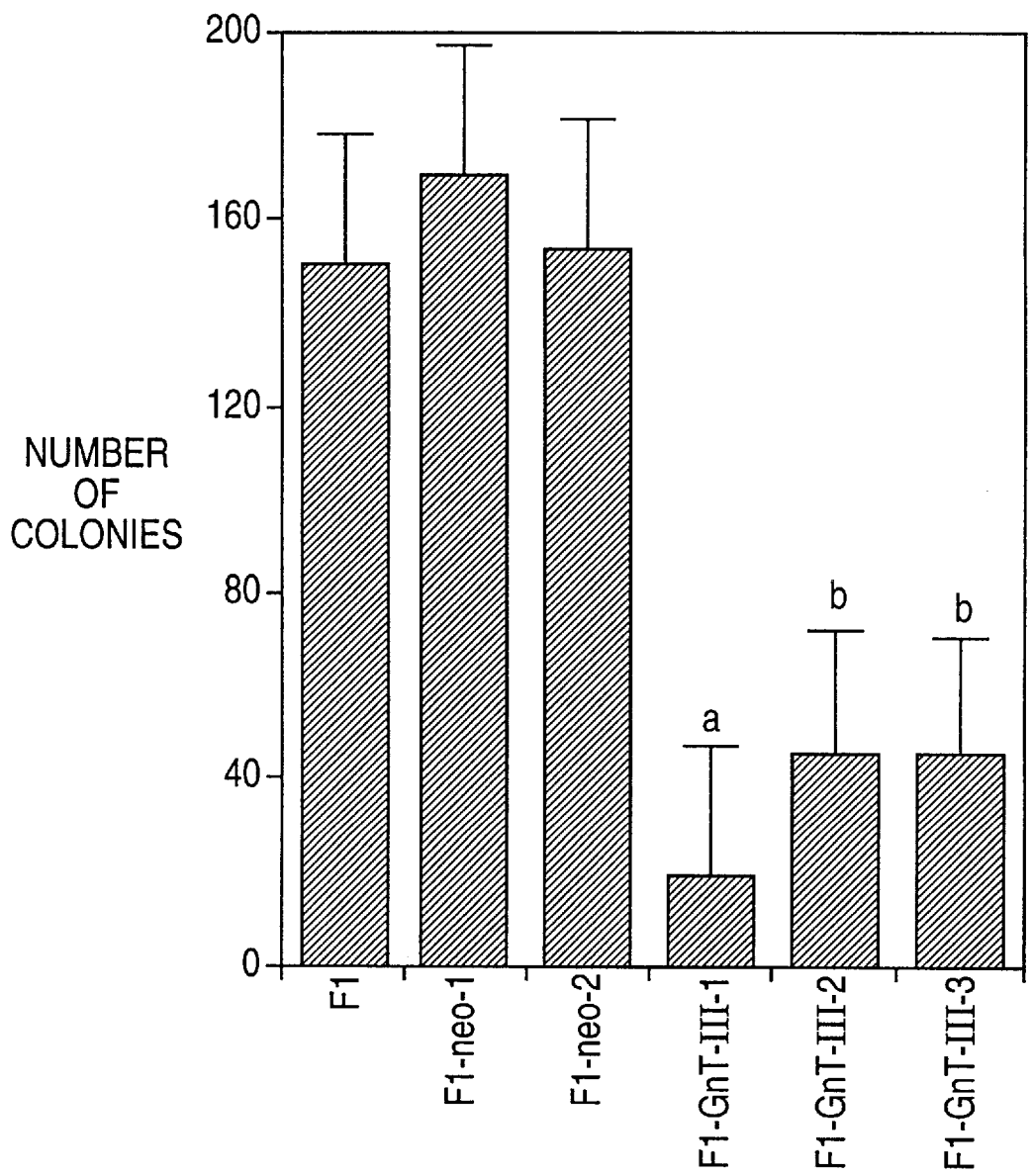
FIG. 6 shows the results of an evaluation of the metastatic potential in vivo.

The abilities of the cells to metastasize in vivo were evaluated in the following manner. The B16-Fl cells and the transformed cells each at the logarithmic growth phase were peeled off the plates by using phosphate-buffered saline (PBS) and the cells were counted. Vital cells were suspended in Hank's buffer and intravenously injected into the tails of a group of seven C57BL/6 mice aged 5 weeks ($3\times10^5$ cells/0.5 ml/animal). After 21 days, the lungs were taken out of the mice and fixed with Bouin's solution and then colonies were counted. FIG. 6 shows the data of the number of colonies. Namely, FIG. 6 shows the results of an evaluation of the ability to metastasize in vivo wherein the ordinate represents the number of colonies and the abscissa represents the cells subjected to the experiment. The bar stands for the average standard error of the data of the experiment repeated thrice. The data were statistically treated in accordance with Student's t test. $^a p<0.01$, $^b p<0.05$ vs. B16-Fl.

When the transformed cells negative to GnT-III were administered, the number of the metastasized colonies were almost the same as that of the parent strain, i.e., the B16-Fl cells. In contrast, the administration of the GnT-III positive cells clearly caused a decrease in the number of the metastasized colonies.

Figure 7:
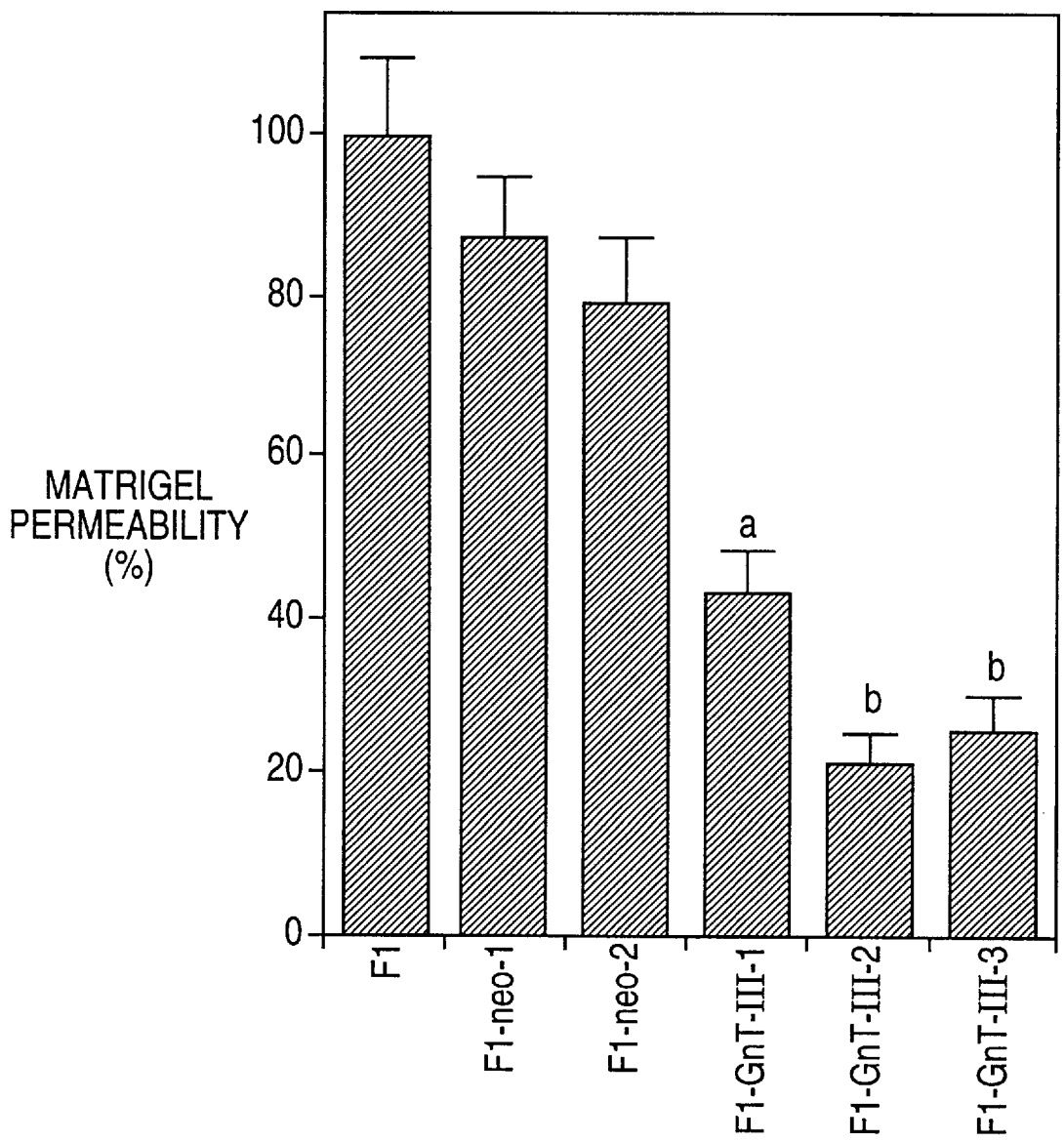
FIG. 7 shows the results of an evaluation of the ability to infiltrate in vitro.

The abilities of the cells to infiltrate in vitro were evaluated by the Matrigel assay method with the use of a Matrigel invasion chamber [BIOCOAT MATRIGEL, mfd. by Becton Dickinson]. FIG. 7 shows the results of an evaluation of the ability to infiltrate in vitro wherein the ordinate represents the number of cells permeating through the Matrigel expressed by taking the data of the B16-Fl cells (i.e., a control) as 100% (average±S.D.) and the abscissa represents the cells subjected to the experiment. The data were statistically treated in accordance with Student's t test. $^a p<0.01$, $^b p<0.05$ vs. B16-Fl.

It has thus been shown that the abilities to infiltrate are also suppressed in the GnT-III positive cells.

Conclusion

According to the present invention, a gene for human GnT-III having an important role in vivo and an industrial process for producing this enzyme are provided. The gene and enzyme are useful in the fields of, for example, biochemistry and diagnosis.

Also, the present invention provides a cancerous metastasis inhibitor comprising GnT-III or a gene thereof, by which the GnT-III activity of cancer cells or the tissues therearound is increased, as the active ingredient. This cancerous metastasis inhibitor is useful in the field of cancer therapy.

Although the present invention has been described in some detail by way of illustration and example for purposes of clarity and understanding, certain obvious modifications can be practiced within the scope of the appended claims.

What is claimed is:

1. An isolated DNA encoding human N-acetylglucosaminyltransferase III (GnT-III).

2. The isolated DNA of claim 1 having the nucleotide sequence of SEQ ID No. 2.

3. An isolated DNA which is hybridizable with the isolated DNA of claim 2 under stringent conditions and which encodes a protein having human GnT-III activity.

4. A recombinant vector which includes the nucleotide sequence of the isolated DNA of claim 1.

5. A transformed host cell which contains the recombinant vector of claim 4.

6. A method of producing human GnT-III which comprises cultivating transformed cells as in claim 5 in a culture medium and isolating human GnT-III from the culture medium.

\* \* \* \* \*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2247 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:1:

```
CCGGCTGCGA  TGCCGGGCGC  CCGCCGCAGC  CGCTGCCGCC  GGAGCCCGGG  ATGGGGCGAG      60

AGGCTGCGGC  GGACGCCAGC  ATCTCCCCGC  CGGGGACCCC  GGGGGCCGCG  GAGCCGCCGC     120

CGCCGCTGCT  GCCGCCGTTG  CTGAGACCCA  GCGGGCGATG  GGATGAAGAT  GAGACGCTAC     180

AAGCTCTTTC  TCATGTTCTG  TATGGCCGGC  CTGTGCCTCA  TCTCCTTCCT  GCACTTCTTC     240

AAGACCCTGT  CCTATGTCAC  CTTCCCCCGA  GAACTGGCCT  CCCTCAGCCC  TAACCTGGTG     300

TCCAGCTTTT  TCTGGAACAA  TGCCCCGGTC  ACGCCCCAGG  CCAGCCCCGA  GCCAGGAGGC     360

CCTGACCTGC  TGCGTACCCC  ACTCTACTCC  CACTCGCCCC  TGCTGCAGCC  GCTGCCGCCC     420

AGCAAGGCGG  CCGAGGAGCT  CCACCGGGTG  GACTTGGTGC  TGCCCGAGGA  CACCACCGAG     480

TATTTCGTGC  GCACCAAGGC  CGGCGGCGTC  TGCTTCAAAC  CCGGCACCAA  GATGCTGGAG     540

AGGCCGCCCC  CGGGACGGCC  GGAGGAGAAG  CCTGAGGGGG  CCAACGGCTC  CTCGGCCCGG     600

CGGCCACCCC  GGTACCTCCT  GAGCGCCCGG  GAGCGCACGG  GGGGCCGAGG  CGCCGGCGC     660

AAGTGGGTGG  AGTGCGTGTG  CCTGCCCGGC  TGGCACGGAC  CCAGCTGCGG  CGTGCCCACT     720
```

| | | | | | |
|---|---|---|---|---|---|
| GTGGTGCAGT | ACTCCAACCT | GCCCACCAAG | GAGCGGCTGG | TGCCCAGGGA | GGTGCCGCGC | 780 |
| CGCGTCATCA | ACGCCATCAA | CGTCAACCAC | GAGTTCGACC | TGCTGGACGT | GCGCTTCCAC | 840 |
| GAGCTGGGCG | ACGTGGTGGA | CGCCTTTGTG | GTGTGCGAGT | CCAACTTCAC | GGCTTATGGG | 900 |
| GAGCCGCGGC | CGCTCAAGTT | CCGGGAGATG | CTGACCAATG | GCACCTTCGA | GTACATCCGC | 960 |
| CACAAGGTGC | TCTATGTCTT | CCTGGACCAC | TTCCCGCCCG | GCGGCCGGCA | GGACGGCTGG | 1020 |
| ATCGCCGACG | ACTACCTGCG | CACCTTCCTC | ACCCAGGACG | GCGTCTCGCG | GCTGCGCAAC | 1080 |
| CTGCGGCCCG | ACGACGTCTT | CATCATTGAC | GATGCGGACG | AGATCCCGGC | CCGTGACGGC | 1140 |
| GTCCTTTTCC | TCAAGCTCTA | CGATGGCTGG | ACCGAGCCCT | TCGCCTTCCA | CATGCGCACG | 1200 |
| TCGCTCTACG | GCTTCTTCTG | GAAGCAGCCG | GGCACCCTGG | AGGTGGTGTC | AGGCTGCACG | 1260 |
| GTGGACATGC | TGCAGGCAGT | GTATGGGCTG | GACGGCATCC | GCCTGCGCCG | CCGCCAGTAC | 1320 |
| TACACCATGC | CCAACTTCAG | ACAGTATGAG | AACCGCACCG | GCCACATCCT | GGTGCAGTGG | 1380 |
| TCGCTGGGCA | GCCCCCTGCA | CTTCGCCGGC | TGGCACTGCT | CCTGGTGCTT | CACGCCCGAG | 1440 |
| GGCATCTACT | TCAAGCTCGT | GTCCGCCCAG | AATGGCGACT | TCCCACGCTG | GGGTGACTAC | 1500 |
| GAGGACAAGC | GGGACCTGAA | CTACATCCGC | GGCCTGATCC | GCACCGGGGG | CTGGTTCGAC | 1560 |
| GGCACGCAGC | AGGAGTACCC | GCCTGCAGAC | CCCAGCGAGC | ACATGTATGC | GCCCAAGTAC | 1620 |
| CTGCTGAAGA | ACTACGACCG | GTTCCACTAC | CTGCTGGACA | CCCCTACCA | GGAGCCCAGG | 1680 |
| AGCACGGCGG | CGGGCGGGTG | GCGCCACAGG | GGTCCCGAGG | GAAGGCCGCC | CGCCCGGGGC | 1740 |
| AAACTGGACG | AGGCGGAAGT | CTAGAGCTGC | ATGATCTGAT | AGGGTTTGTG | ACAGGGCGGG | 1800 |
| GGTGGCGGCG | GCCCCTAGCG | CTATCTCCCT | GCCTCCTGCC | GGCTCCTTGG | TTCTTGAGGG | 1860 |
| GACCAGGAGT | GGGTGGGGAG | TGGGGGTGGG | GCTAGGGTTT | CCCTACTGAA | GCCCTTGTGA | 1920 |
| TCAAGGGTCA | GGCCTTTGAG | CTCAGAAAAT | ATCCCTCCTG | TTGGGAGAGG | GCGCAGGCCG | 1980 |
| TGACGTCTGG | GTGGCCCTTA | TGACTGCCAA | GACTGCTGTG | GCCAGGAGGT | GCCACTGGAG | 2040 |
| TGTGCGTGGT | GGTCCCTGGG | TAGCGGGGGA | GGGTAGGCAG | GATTGGGGAA | GAGAGCCTGC | 2100 |
| AGGATCTCAC | CAGGCAGCCT | CTGGGGGGTG | GCCAGGCCGG | AAAAAGCCCA | CCATTTGGCA | 2160 |
| TCCCTGGGCC | TTGGGCTCCG | TGTGGGAGAC | CGGCCTGCCA | GGAGGACCCA | GGGCTCTGTA | 2220 |
| AGTAGATGCA | TTTGGGTCCA | GGAGGAA | | | | 2247 |

(2) INFORMATION FOR SEQ ID NO:2:

(i) SEQUENCE CHARACTERISTICS:
        (A) LENGTH: 1593 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

```
ATG  AGA  CGC  TAC  AAG  CTC  TTT  CTC  ATG  TTC  TGT  ATG  GCC  GGC  CTG            45
Met  Arg  Arg  Tyr  Lys  Leu  Phe  Leu  Met  Phe  Cys  Met  Ala  Gly  Leu
 1              5                        10                       15

TGC  CTC  ATC  TCC  TTC  CTG  CAC  TTC  TTC  AAG  ACC  CTG  TCC  TAT  GTC            90
Cys  Leu  Ile  Ser  Phe  Leu  His  Phe  Phe  Lys  Thr  Leu  Ser  Tyr  Val
                20                       25                       30

ACC  TTC  CCC  CGA  GAA  CTG  GCC  TCC  CTC  AGC  CCT  AAC  CTG  GTG  TCC           135
Thr  Phe  Pro  Arg  Glu  Leu  Ala  Ser  Leu  Ser  Pro  Asn  Leu  Val  Ser
                35                       40                       45

AGC  TTT  TTC  TGG  AAC  AAT  GCC  CCG  GTC  ACG  CCC  CAG  GCC  AGC  CCC           180
Ser  Phe  Phe  Trp  Asn  Asn  Ala  Pro  Val  Thr  Pro  Gln  Ala  Ser  Pro
                50                       55                       60
```

| | | | | | | | | | | | | | | | |
|---|---|---|---|---|---|---|---|---|---|---|---|---|---|---|---|
| GAG | CCA | GGA | GGC | CCT | GAC | CTG | CTG | CGT | ACC | CCA | CTC | TAC | TCC | CAC | 225 |
| Glu | Pro | Gly | Gly | Pro | Asp | Leu | Leu | Arg | Thr | Pro | Leu | Tyr | Ser | His | |
| | | | | 65 | | | | 70 | | | | | | 75 | |
| TCG | CCC | CTG | CTG | CAG | CCG | CTG | CCG | CCC | AGC | AAG | GCG | GCC | GAG | GAG | 270 |
| Ser | Pro | Leu | Leu | Gln | Pro | Leu | Pro | Pro | Ser | Lys | Ala | Ala | Glu | Glu | |
| | | | | 80 | | | | | 85 | | | | | 90 | |
| CTC | CAC | CGG | GTG | GAC | TTG | GTG | CTG | CCC | GAG | GAC | ACC | ACC | GAG | TAT | 315 |
| Leu | His | Arg | Val | Asp | Leu | Val | Leu | Pro | Glu | Asp | Thr | Thr | Glu | Tyr | |
| | | | | 95 | | | | | 100 | | | | | 105 | |
| TTC | GTG | CGC | ACC | AAG | GCC | GGC | GGC | GTC | TGC | TTC | AAA | CCC | GGC | ACC | 360 |
| Phe | Val | Arg | Thr | Lys | Ala | Gly | Gly | Val | Cys | Phe | Lys | Pro | Gly | Thr | |
| | | | | 110 | | | | | 115 | | | | | 120 | |
| AAG | ATG | CTG | GAG | AGG | CCG | CCC | CCG | GGA | CGG | CCG | GAG | GAG | AAG | CCT | 405 |
| Lys | Met | Leu | Glu | Arg | Pro | Pro | Pro | Gly | Arg | Pro | Glu | Glu | Lys | Pro | |
| | | | | 125 | | | | | 130 | | | | | 135 | |
| GAG | GGG | GCC | AAC | GGC | TCC | TCG | GCC | CGG | CGG | CCA | CCC | CGG | TAC | CTC | 450 |
| Glu | Gly | Ala | Asn | Gly | Ser | Ser | Ala | Arg | Arg | Pro | Pro | Arg | Tyr | Leu | |
| | | | | 140 | | | | | 145 | | | | | 150 | |
| CTG | AGC | GCC | CGG | GAG | CGC | ACG | GGG | GGC | CGA | GGC | GCC | CGG | CGC | AAG | 495 |
| Leu | Ser | Ala | Arg | Glu | Arg | Thr | Gly | Gly | Arg | Gly | Ala | Arg | Arg | Lys | |
| | | | | 155 | | | | | 160 | | | | | 165 | |
| TGG | GTG | GAG | TGC | GTG | TGC | CTG | CCC | GGC | TGG | CAC | GGA | CCC | AGC | TGC | 540 |
| Trp | Val | Glu | Cys | Val | Cys | Leu | Pro | Gly | Trp | His | Gly | Pro | Ser | Cys | |
| | | | | 170 | | | | | 175 | | | | | 180 | |
| GGC | GTG | CCC | ACT | GTG | GTG | CAG | TAC | TCC | AAC | CTG | CCC | ACC | AAG | GAG | 585 |
| Gly | Val | Pro | Thr | Val | Val | Gln | Tyr | Ser | Asn | Leu | Pro | Thr | Lys | Glu | |
| | | | | 185 | | | | | 190 | | | | | 195 | |
| CGG | CTG | GTG | CCC | AGG | GAG | GTG | CCG | CGC | CGC | GTC | ATC | AAC | GCC | ATC | 630 |
| Arg | Leu | Val | Pro | Arg | Glu | Val | Pro | Arg | Arg | Val | Ile | Asn | Ala | Ile | |
| | | | | 200 | | | | | 205 | | | | | 210 | |
| AAC | GTC | AAC | CAC | GAG | TTC | GAC | CTG | CTG | GAC | GTG | CGC | TTC | CAC | GAG | 675 |
| Asn | Val | Asn | His | Glu | Phe | Asp | Leu | Leu | Asp | Val | Arg | Phe | His | Glu | |
| | | | | 215 | | | | | 220 | | | | | 225 | |
| CTG | GGC | GAC | GTG | GTG | GAC | GCC | TTT | GTG | GTG | TGC | GAG | TCC | AAC | TTC | 720 |
| Leu | Gly | Asp | Val | Val | Asp | Ala | Phe | Val | Val | Cys | Glu | Ser | Asn | Phe | |
| | | | | 230 | | | | | 235 | | | | | 240 | |
| ACG | GCT | TAT | GGG | GAG | CCG | CGG | CCG | CTC | AAG | TTC | CGG | GAG | ATG | CTG | 765 |
| Thr | Ala | Tyr | Gly | Glu | Pro | Arg | Pro | Leu | Lys | Phe | Arg | Glu | Met | Leu | |
| | | | | 245 | | | | | 250 | | | | | 255 | |
| ACC | AAT | GGC | ACC | TTC | GAG | TAC | ATC | CGC | CAC | AAG | GTG | CTC | TAT | GTC | 810 |
| Thr | Asn | Gly | Thr | Phe | Glu | Tyr | Ile | Arg | His | Lys | Val | Leu | Tyr | Val | |
| | | | | 260 | | | | | 265 | | | | | 270 | |
| TTC | CTG | GAC | CAC | TTC | CCG | CCC | GGC | GGC | CGG | CAG | GAC | GGC | TGG | ATC | 855 |
| Phe | Leu | Asp | His | Phe | Pro | Pro | Gly | Gly | Arg | Gln | Asp | Gly | Trp | Ile | |
| | | | | 275 | | | | | 280 | | | | | 285 | |
| GCC | GAC | GAC | TAC | CTG | CGC | ACC | TTC | CTC | ACC | CAG | GAC | GGC | GTC | TCG | 900 |
| Ala | Asp | Asp | Tyr | Leu | Arg | Thr | Phe | Leu | Thr | Gln | Asp | Gly | Val | Ser | |
| | | | | 290 | | | | | 295 | | | | | 300 | |
| CGG | CTG | CGC | AAC | CTG | CGG | CCC | GAC | GAC | GTC | TTC | ATC | ATT | GAC | GAT | 945 |
| Arg | Leu | Arg | Asn | Leu | Arg | Pro | Asp | Asp | Val | Phe | Ile | Ile | Asp | Asp | |
| | | | | 305 | | | | | 310 | | | | | 315 | |
| GCG | GAC | GAG | ATC | CCG | GCC | CGT | GAC | GGC | GTC | CTT | TTC | CTC | AAG | CTC | 990 |
| Ala | Asp | Glu | Ile | Pro | Ala | Arg | Asp | Gly | Val | Leu | Phe | Leu | Lys | Leu | |
| | | | | 320 | | | | | 325 | | | | | 330 | |
| TAC | GAT | GGC | TGG | ACC | GAG | CCC | TTC | GCC | TTC | CAC | ATG | CGC | ACG | TCG | 1035 |
| Tyr | Asp | Gly | Trp | Thr | Glu | Pro | Phe | Ala | Phe | His | Met | Arg | Thr | Ser | |
| | | | | 335 | | | | | 340 | | | | | 345 | |
| CTC | TAC | GGC | TTC | TTC | TGG | AAG | CAG | CCG | GGC | ACC | CTG | GAG | GTG | GTG | 1080 |
| Leu | Tyr | Gly | Phe | Phe | Trp | Lys | Gln | Pro | Gly | Thr | Leu | Glu | Val | Val | |
| | | | | 350 | | | | | 355 | | | | | 360 | |

| | | | | | | | | | | | | | | | |
|---|---|---|---|---|---|---|---|---|---|---|---|---|---|---|---|
| TCA | GGC | TGC | ACG | GTG | GAC | ATG | CTG | CAG | GCA | GTG | TAT | GGG | CTG | GAC | 1125 |
| Ser | Gly | Cys | Thr | Val | Asp | Met | Leu | Gln | Ala | Val | Tyr | Gly | Leu | Asp | |
| | | | 365 | | | | | 370 | | | | | | 375 | |
| GGC | ATC | CGC | CTG | CGC | CGC | CGC | CAG | TAC | TAC | ACC | ATG | CCC | AAC | TTC | 1170 |
| Gly | Ile | Arg | Leu | Arg | Arg | Arg | Gln | Tyr | Tyr | Thr | Met | Pro | Asn | Phe | |
| | | | | 380 | | | | | 385 | | | | | 390 | |
| AGA | CAG | TAT | GAG | AAC | CGC | ACC | GGC | CAC | ATC | CTG | GTG | CAG | TGG | TCG | 1215 |
| Arg | Gln | Tyr | Glu | Asn | Arg | Thr | Gly | His | Ile | Leu | Val | Gln | Trp | Ser | |
| | | | | 395 | | | | | 400 | | | | | 405 | |
| CTG | GGC | AGC | CCC | CTG | CAC | TTC | GCC | GGC | TGG | CAC | TGC | TCC | TGG | TGC | 1260 |
| Leu | Gly | Ser | Pro | Leu | His | Phe | Ala | Gly | Trp | His | Cys | Ser | Trp | Cys | |
| | | | | 410 | | | | | 415 | | | | | 420 | |
| TTC | ACG | CCC | GAG | GGC | ATC | TAC | TTC | AAG | CTC | GTG | TCC | GCC | CAG | AAT | 1305 |
| Phe | Thr | Pro | Glu | Gly | Ile | Tyr | Phe | Lys | Leu | Val | Ser | Ala | Gln | Asn | |
| | | | | 425 | | | | | 430 | | | | | 435 | |
| GGC | GAC | TTC | CCA | CGC | TGG | GGT | GAC | TAC | GAG | GAC | AAG | CGG | GAC | CTG | 1350 |
| Gly | Asp | Phe | Pro | Arg | Trp | Gly | Asp | Tyr | Glu | Asp | Lys | Arg | Asp | Leu | |
| | | | | 440 | | | | | 445 | | | | | 450 | |
| AAC | TAC | ATC | CGC | GGC | CTG | ATC | CGC | ACC | GGG | GGC | TGG | TTC | GAC | GGC | 1395 |
| Asn | Tyr | Ile | Arg | Gly | Leu | Ile | Arg | Thr | Gly | Gly | Trp | Phe | Asp | Gly | |
| | | | | 455 | | | | | 460 | | | | | 465 | |
| ACG | CAG | CAG | GAG | TAC | CCG | CCT | GCA | GAC | CCC | AGC | GAG | CAC | ATG | TAT | 1440 |
| Thr | Gln | Gln | Glu | Tyr | Pro | Pro | Ala | Asp | Pro | Ser | Glu | His | Met | Tyr | |
| | | | | 470 | | | | | 475 | | | | | 480 | |
| GCG | CCC | AAG | TAC | CTG | CTG | AAG | AAC | TAC | GAC | CGG | TTC | CAC | TAC | CTG | 1485 |
| Ala | Pro | Lys | Tyr | Leu | Leu | Lys | Asn | Tyr | Asp | Arg | Phe | His | Tyr | Leu | |
| | | | | 485 | | | | | 490 | | | | | 495 | |
| CTG | GAC | AAC | CCC | TAC | CAG | GAG | CCC | AGG | AGC | ACG | GCG | GCG | GGC | GGG | 1530 |
| Leu | Asp | Asn | Pro | Tyr | Gln | Glu | Pro | Arg | Ser | Thr | Ala | Ala | Gly | Gly | |
| | | | | 500 | | | | | 505 | | | | | 510 | |
| TGG | CGC | CAC | AGG | GGT | CCC | GAG | GGA | AGG | CCG | CCC | GCC | CGG | GGC | AAA | 1575 |
| Trp | Arg | His | Arg | Gly | Pro | Glu | Gly | Arg | Pro | Pro | Ala | Arg | Gly | Lys | |
| | | | | 515 | | | | | 520 | | | | | 525 | |
| CTG | GAC | GAG | GCG | GAA | GTC | | | | | | | | | | 1593 |
| Leu | Asp | Glu | Ala | Glu | Val | | | | | | | | | | |
| | | | | 530 | | | | | | | | | | | |

( 2 ) INFORMATION FOR SEQ ID NO:3:

( i ) SEQUENCE CHARACTERISTICS:
        ( A ) LENGTH: 1608 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i x ) SEQUENCE DESCRIPTION: SEQ ID NO: 3:

| | | | | | | | | | | | | | | | |
|---|---|---|---|---|---|---|---|---|---|---|---|---|---|---|---|
| ATG | AGA | CGC | TAC | AAG | CTT | TTT | CTC | ATG | TTC | TGT | ATG | GCC | GGC | CTG | 45 |
| Met | Arg | Arg | Tyr | Lys | Leu | Phe | Leu | Met | Phe | Cys | Met | Ala | Gly | Leu | |
| 1 | | | | 5 | | | | | 10 | | | | | 15 | |
| TGC | CTC | ATC | TCC | TTC | CTG | CAC | TTC | TTT | AAG | ACG | TTA | TCC | TAT | GTC | 90 |
| Cys | Leu | Ile | Ser | Phe | Leu | His | Phe | Phe | Lys | Thr | Leu | Ser | Tyr | Val | |
| | | | | 20 | | | | | 25 | | | | | 30 | |
| ACC | TTC | CCG | AGA | GAA | CTG | GCC | TCC | CTC | AGC | CCT | AAC | CTC | ATA | TCC | 135 |
| Thr | Phe | Pro | Arg | Glu | Leu | Ala | Ser | Leu | Ser | Pro | Asn | Leu | Ile | Ser | |
| | | | | 35 | | | | | 40 | | | | | 45 | |
| AGC | TTC | TTC | TGG | AAC | AAT | GCC | CCT | GTC | ACT | CCC | CAG | GCC | AGT | CCG | 180 |
| Ser | Phe | Phe | Trp | Asn | Asn | Ala | Pro | Val | Thr | Pro | Gln | Ala | Ser | Pro | |
| | | | | 50 | | | | | 55 | | | | | 60 | |
| GAG | CCC | GGT | GAC | CCC | GAC | TTG | TTA | CGG | ACT | CCA | CTC | TAC | TCC | CAC | 225 |
| Glu | Pro | Gly | Asp | Pro | Asp | Leu | Leu | Arg | Thr | Pro | Leu | Tyr | Ser | His | |

```
                          65                           70                           75
TCC  CCC  CTG  CTC  CAG  CCA  CTG  TCC  CCT  AGC  AAG  GCC  ACC  GAA  GAA       270
Ser  Pro  Leu  Leu  Gln  Pro  Leu  Ser  Pro  Ser  Lys  Ala  Thr  Glu  Glu
                    80                       85                       90

CTG  CAC  CGG  GTG  GAC  TTC  GTG  TTG  CCG  GAG  GAC  ACC  ACA  GAG  TAT       315
Leu  His  Arg  Val  Asp  Phe  Val  Leu  Pro  Glu  Asp  Thr  Thr  Glu  Tyr
                    95                      100                      105

TTT  GTG  CGC  ACC  AAA  GCT  GGC  GGT  GTG  TGC  TTC  AAA  CCA  GGT  ACC       360
Phe  Val  Arg  Thr  Lys  Ala  Gly  Gly  Val  Cys  Phe  Lys  Pro  Gly  Thr
                   110                      115                      120

AGG  ATG  CTG  GAG  AAA  CCT  TCT  CCA  GGG  CGG  ACA  GAG  GAG  AAG  ACC       405
Arg  Met  Leu  Glu  Lys  Pro  Ser  Pro  Gly  Arg  Thr  Glu  Glu  Lys  Thr
                   125                      130                      135

AAG  GTG  GCT  GAG  GGG  TCC  TCG  GTC  CGG  GGT  CCT  GCT  CGG  AGG  CCT       450
Lys  Val  Ala  Glu  Gly  Ser  Ser  Val  Arg  Gly  Pro  Ala  Arg  Arg  Pro
                   140                      145                      150

ATG  CGG  CAT  GTG  TTG  AGT  GCA  CGG  GAG  CGC  CTG  GGA  GGC  CGG  GGC       495
Met  Arg  His  Val  Leu  Ser  Ala  Arg  Glu  Arg  Leu  Gly  Gly  Arg  Gly
                   155                      160                      165

ACT  AGG  CGC  AAG  TGG  GTT  GAG  TGT  GTG  TGC  CTG  CCA  GGC  TGG  CAC       540
Thr  Arg  Arg  Lys  Trp  Val  Glu  Cys  Val  Cys  Leu  Pro  Gly  Trp  His
                   170                      175                      180

GGG  CCC  AGC  TGC  GGG  GTG  CCC  ACT  GTG  GTC  CAG  TAT  TCC  AAC  CTG       585
Gly  Pro  Ser  Cys  Gly  Val  Pro  Thr  Val  Val  Gln  Tyr  Ser  Asn  Leu
                   185                      190                      195

CCC  ACC  AAG  GAG  CGC  CTG  GTA  CCC  AGG  GAG  GTG  CCG  AGG  CGG  GTT       630
Pro  Thr  Lys  Glu  Arg  Leu  Val  Pro  Arg  Glu  Val  Pro  Arg  Arg  Val
                   200                      205                      210

ATC  AAC  GCC  ATC  AAC  ATC  AAC  CAT  GAG  TTC  GAC  CTG  CTG  GAT  GTG       675
Ile  Asn  Ala  Ile  Asn  Ile  Asn  His  Glu  Phe  Asp  Leu  Leu  Asp  Val
                   215                      220                      225

CGC  TTC  CAT  GAG  CTG  GGC  GAT  GTT  GTG  GAC  GCC  TTT  GTG  GTC  TGC       720
Arg  Phe  His  Glu  Leu  Gly  Asp  Val  Val  Asp  Ala  Phe  Val  Val  Cys
                   230                      235                      240

GAA  TCC  AAT  TTC  ACC  GCC  TAC  GGG  GAG  CCT  CGG  CCG  CTC  AAG  TTC       765
Glu  Ser  Asn  Phe  Thr  Ala  Tyr  Gly  Glu  Pro  Arg  Pro  Leu  Lys  Phe
                   245                      250                      255

CGA  GAG  ATG  CTG  ACC  AAT  GGC  ACC  TTC  GAG  TAC  ATC  CGC  CAC  AAG       810
Arg  Glu  Met  Leu  Thr  Asn  Gly  Thr  Phe  Glu  Tyr  Ile  Arg  His  Lys
                   260                      265                      270

GTG  CTC  TAC  GTC  TTC  CTG  GAC  CAC  TTC  CCA  CCT  GGT  GGC  CGT  CAG       855
Val  Leu  Tyr  Val  Phe  Leu  Asp  His  Phe  Pro  Pro  Gly  Gly  Arg  Gln
                   275                      280                      285

GAC  GGC  TGG  ATT  GCA  GAC  GAC  TAC  CTG  CGT  ACC  TTC  CTC  ACC  CAG       900
Asp  Gly  Trp  Ile  Ala  Asp  Asp  Tyr  Leu  Arg  Thr  Phe  Leu  Thr  Gln
                   290                      295                      300

GAT  GGT  GTC  TCC  CGC  CTG  CGC  AAC  CTG  CGA  CCT  GAT  GAC  GTC  TTT       945
Asp  Gly  Val  Ser  Arg  Leu  Arg  Asn  Leu  Arg  Pro  Asp  Asp  Val  Phe
                   305                      310                      315

ATC  ATC  GAC  GAC  GCG  GAC  GAG  ATC  CCT  GCG  CGT  GAT  GGT  GTG  CTG       990
Ile  Ile  Asp  Asp  Ala  Asp  Glu  Ile  Pro  Ala  Arg  Asp  Gly  Val  Leu
                   320                      325                      330

TTC  CTC  AAG  CTC  TAC  GAT  GGC  TGG  ACA  GAG  CCC  TTC  GCC  TTC  CAT      1035
Phe  Leu  Lys  Leu  Tyr  Asp  Gly  Trp  Thr  Glu  Pro  Phe  Ala  Phe  His
                   335                      340                      345

ATG  CGC  AAG  TCC  CTG  TAT  GGT  TTC  TTT  TGG  AAG  CAA  CCA  GGC  ACA      1080
Met  Arg  Lys  Ser  Leu  Tyr  Gly  Phe  Phe  Trp  Lys  Gln  Pro  Gly  Thr
                   350                      355                      360

CTG  GAG  GTG  GTG  TCA  GGC  TGC  ACC  ATT  GAC  ATG  CTG  CAG  GCT  GTG      1125
Leu  Glu  Val  Val  Ser  Gly  Cys  Thr  Ile  Asp  Met  Leu  Gln  Ala  Val
```

|  |  |  |  |  |  |  |  |  |  |  |  |  |  |  |  |
|---|---|---|---|---|---|---|---|---|---|---|---|---|---|---|---|
|  |  |  |  | 365 |  |  |  | 370 |  |  |  |  | 375 |  |  |
| TAT | GGG | CTG | GAC | GGC | ATC | CGC | CTG | CGC | CGC | CGT | CAG | TAC | TAC | ACC | 1170 |
| Tyr | Gly | Leu | Asp | Gly | Ile | Arg | Leu | Arg | Arg | Arg | Gln | Tyr | Tyr | Thr |  |
|  |  |  |  | 380 |  |  |  | 385 |  |  |  |  | 390 |  |  |
| ATG | CCC | AAC | TTT | CGA | CAG | TAT | GAG | AAC | CGC | ACC | GGC | CAC | ATC | CTA | 1215 |
| Met | Pro | Asn | Phe | Arg | Gln | Tyr | Glu | Asn | Arg | Thr | Gly | His | Ile | Leu |  |
|  |  |  |  | 395 |  |  |  | 400 |  |  |  |  | 405 |  |  |
| GTG | CAG | TGG | TCT | CTC | GGC | AGC | CCC | CTG | CAC | TTC | GCG | GGC | TGG | CAC | 1260 |
| Val | Gln | Trp | Ser | Leu | Gly | Ser | Pro | Leu | His | Phe | Ala | Gly | Trp | His |  |
|  |  |  |  | 410 |  |  |  | 415 |  |  |  |  | 420 |  |  |
| TGC | TCC | TGG | TGC | TTC | ACA | CCC | GAG | GGC | ATC | TAC | TTC | AAA | CTC | GTG | 1305 |
| Cys | Ser | Trp | Cys | Phe | Thr | Pro | Glu | Gly | Ile | Tyr | Phe | Lys | Leu | Val |  |
|  |  |  |  | 425 |  |  |  | 430 |  |  |  |  | 435 |  |  |
| TCG | GCC | CAG | AAT | GGT | GAC | TTC | CCC | CGC | TGG | GGT | GAC | TAC | GAG | GAC | 1350 |
| Ser | Ala | Gln | Asn | Gly | Asp | Phe | Pro | Arg | Trp | Gly | Asp | Tyr | Glu | Asp |  |
|  |  |  |  | 440 |  |  |  | 445 |  |  |  |  | 450 |  |  |
| AAG | AGG | GAC | CTC | AAT | TAC | ATC | CGA | AGC | TTG | ATT | CGC | ACT | GGG | GGA | 1395 |
| Lys | Arg | Asp | Leu | Asn | Tyr | Ile | Arg | Ser | Leu | Ile | Arg | Thr | Gly | Gly |  |
|  |  |  |  | 455 |  |  |  | 460 |  |  |  |  | 465 |  |  |
| TGG | TTC | GAC | GGC | ACG | CAG | CAG | GAG | TAC | CCT | CCT | GCA | GAC | CCC | AGT | 1440 |
| Trp | Phe | Asp | Gly | Thr | Gln | Gln | Glu | Tyr | Pro | Pro | Ala | Asp | Pro | Ser |  |
|  |  |  |  | 470 |  |  |  | 475 |  |  |  |  | 480 |  |  |
| GAA | CAC | ATG | TAT | GCT | CCT | AAG | TAC | CTG | CTC | AAG | AAC | TAT | GAC | CAG | 1485 |
| Glu | His | Met | Tyr | Ala | Pro | Lys | Tyr | Leu | Leu | Lys | Asn | Tyr | Asp | Gln |  |
|  |  |  |  | 485 |  |  |  | 490 |  |  |  |  | 495 |  |  |
| TTC | CGC | TAC | TTG | CTC | GAA | AAT | CCC | TAC | CGG | GAG | CCC | AAG | AGC | ACT | 1530 |
| Phe | Arg | Tyr | Leu | Leu | Glu | Asn | Pro | Tyr | Arg | Glu | Pro | Lys | Ser | Thr |  |
|  |  |  |  | 500 |  |  |  | 505 |  |  |  |  | 510 |  |  |
| GTA | GAG | GGT | GGG | CGC | CGG | AAC | CAG | GGC | TCA | GAC | GGA | AGG | TCA | TCT | 1575 |
| Val | Glu | Gly | Gly | Arg | Arg | Asn | Gln | Gly | Ser | Asp | Gly | Arg | Ser | Ser |  |
|  |  |  |  | 515 |  |  |  | 520 |  |  |  |  | 525 |  |  |
| GCT | GTC | AGG | GGC | AAG | TTG | GAT | ACA | ACG | GAG | GGC |  |  |  |  | 1608 |
| Ala | Val | Arg | Gly | Lys | Leu | Asp | Thr | Thr | Glu | Gly |  |  |  |  |  |
|  |  |  |  | 530 |  |  |  | 535 |  |  |  |  |  |  |  |